United States Patent [19]

Vcelka

[11] 4,318,812

[45] Mar. 9, 1982

[54] COMPACT FILTER

[75] Inventor: John L. Vcelka, Zion, Ill.

[73] Assignee: Abbott Laboratories, North Chicago, Ill.

[21] Appl. No.: 190,115

[22] Filed: Sep. 24, 1980

[51] Int. Cl.³ ............................................. B01D 35/02
[52] U.S. Cl. .................................. 210/323.2; 210/446; 210/927; 264/27
[58] Field of Search ............... 55/363; 210/323.2, 342, 210/448, 927, 446; 264/27; 156/73.1, 204; 128/214 R, 214 C

[56] References Cited

U.S. PATENT DOCUMENTS

| | | | |
|---|---|---|---|
| 1,810,965 | 6/1931 | Hopkins | 210/323.1 |
| 2,016,161 | 10/1935 | Wilderman | 210/448 |
| 2,079,366 | 5/1937 | Thomas | 210/164 |
| 3,217,889 | 11/1965 | Berg | 210/448 |
| 3,557,786 | 1/1971 | Barr, Sr. et al. | 210/927 X |
| 4,081,379 | 3/1978 | Smith | 210/342 X |

FOREIGN PATENT DOCUMENTS 1005378  3/1957  Fed. Rep. of Germany ........ 55/363

Primary Examiner—Frank A. Spear, Jr.
Attorney, Agent, or Firm—Robert L. Niblack; Neil E. Hamilton

[57] ABSTRACT

A high volume filter for use in an I.V. or blood administration set. A double filter unit is formed by folding a length of filter material into two portions to form pocket members with tubular inlets placed in each. These components are then sealed into a length of plastic tubing with an additional tubular member to form a filter unit. In a preferred embodiment, the filter unit is formed integrally with a drip chamber.

15 Claims, 13 Drawing Figures

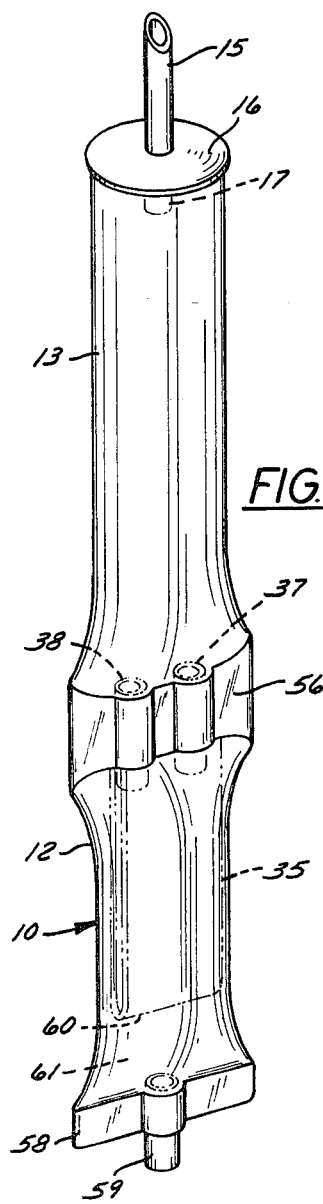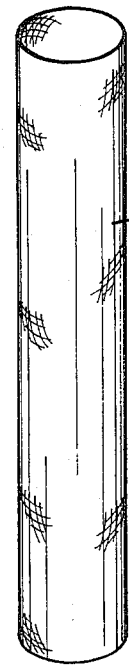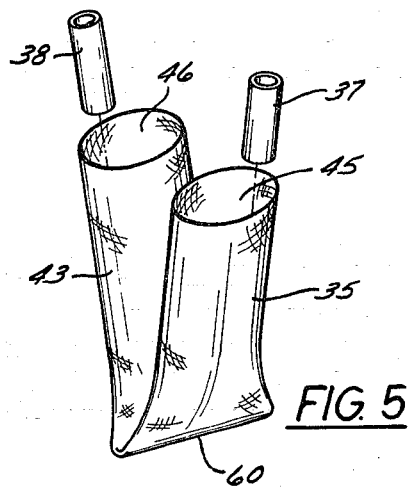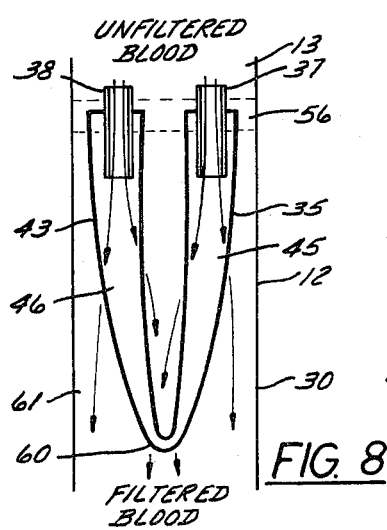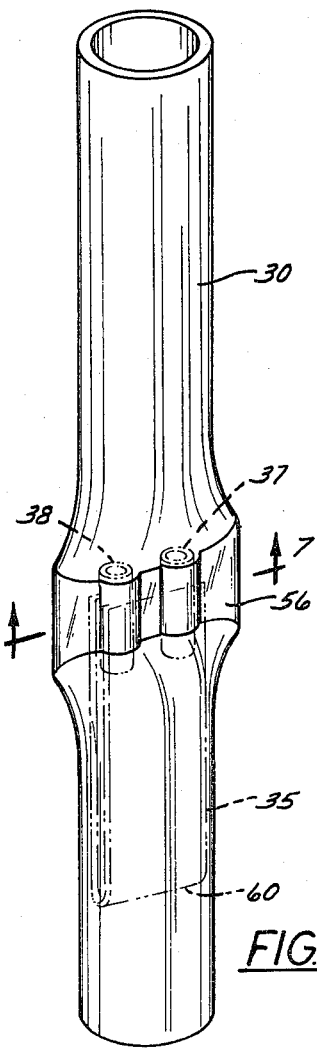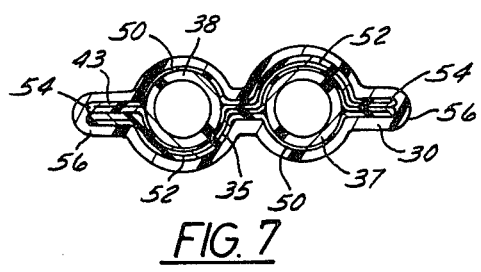

COMPACT FILTER

BACKGROUND OF THE INVENTION

This invention relates to a high capacity compact filter for the filtration of parenteral solutions including blood. More particularly it relates to a filter which by means of its construction can filter a volume of liquid at least twice the capacity of another filter of the same length.

In the I.V. and blood administration field there is a need for filter units which not only will provide the usual filtering effect but also those which can effect filtration and do so at as high capacity as possible. The capacity of a filter unit is important in parenteral solutions or blood administration sets in that they are disposable. Consequently, the least amount of material which is required for their manufacture will result in a lower cost. A blood filter generally of the type concerned with in this invention is described in U.S. Pat. No. 3,217,889. Filters providing a high degree of contact between a filter element and the material to be filtered are described in U.S. Pat. No. 2,016,116 and U.S. Pat. No. 2,079,366.

Nowhere in the prior art is there provided a filter unit specifically constructed for use in the filtering of parenteral solutions or blood wherein two filter units are in effect formed in a side-by-side relationship so that a high capacity filter unit results. Neither is there provided a filter unit which is easily sterilized and can be composed of plastic material so as to be disposable. The filter unit of this invention is also easily manufactured and lends itself to being formed as a component part of a combined drip chamber and filter unit.

It is an advantage of the present invention to provide a novel filter for an I.V. or blood administration set. Other advantages are a filter unit which is compact, has a high capacity flow rate, can be composed of relatively inexpensive materials, yet can be sterilized. The filter unit of this invention also lends itself to being easily fabricated into units normally employed in conjunction with a blood or parenteral solution administration set such as a drip chamber.

SUMMARY OF THE INVENTION

The foregoing advantages are accomplished and the shortcomings of the prior art are overcome by the present high capacity, compact filter wherein two filter units are positioned in substantially a side by side relationship and joined by a common wall member. A fluid entrance passageway is in fluid communication with each filter unit and closure means are provided to seal the passage members in the filter units. A fluid outlet passage member is also in fluid communication with the closure means. The filter units are formed from a folded tubular mesh material with the fluid entrance passage members being formed from flexible tubular members.

In a preferred embodiment, the closure means defines a compartment opposite the passage members and in communication with the fluid outlet passage member. In one embodiment, a drip chamber surrounds the first and second fluid passage members in the fluid-tight manner with a single seal defining the attachment of the filter units to the fluid passage members and forming the bottom of the drip chamber.

A method of manufacturing the high capacity compact filter is also provided wherein a tubular filter material of the mesh type is folded to provided two filter pocket members positioned substantially in a side-by-side relationship. A tubular fluid passage member is inserted into each filter pocket. The folded tubular filter material with the fluid passage members is placed into a length of flexible tubular plastic material and an additional tubular fluid passage member is inserted into the length of flexible plastic material at the end opposite the two fluid passage members. Compressive sealing is effected to seal the opposing ends of the tubular plastic material at a point where the tubular passage members contact the flexible tubular material. This seals the tubular fluid passage members and the filter material at one end of the tubular plastic material and the additional fluid passage member at the opposing end thereof thus forming a closure for the filter unit. In one manner, the tubular filter is folded into two substantially equal lengths with a common crease approximately midway between the ends thereof. In another manner, the tubular filter is folded in an inverted manner with one end of the filter material being drawn inside the tubular filter and all of the open ends placed adjacent to each other so as to result in two filter pockets of substantially the same dimension. The preferred manner of compressive sealing the filter material and the tubular passage members into the length of flexible plastic material is by Radio Frequency sealing.

BRIEF DESCRIPTION OF THE DRAWINGS

A better understanding of the compact filter unit of this invention will be afforded by reference to the drawing wherein:

FIG. 3 is a perspective view showing the combined filter and drip chamber unit of this invention.

FIG. 4 is a perspective view of a length of tubular filter material employed in the manufacture of the filter unit shown in FIG. 3.

FIG. 5 is an assembly view illustrating one step in the process of manufacturing the filter unit.

FIG. 6 is an assembly view illustrating still a further step in the assembly of the filter unit.

FIG. 7 is a view in horizontal section taken along line 7—7 of FIG. 6.

FIG. 8 is a view in vertical section illustrating the flow path of liquid through the filter unit.

DESCRIPTION OF ONE EMBODIMENT

Figure 1:
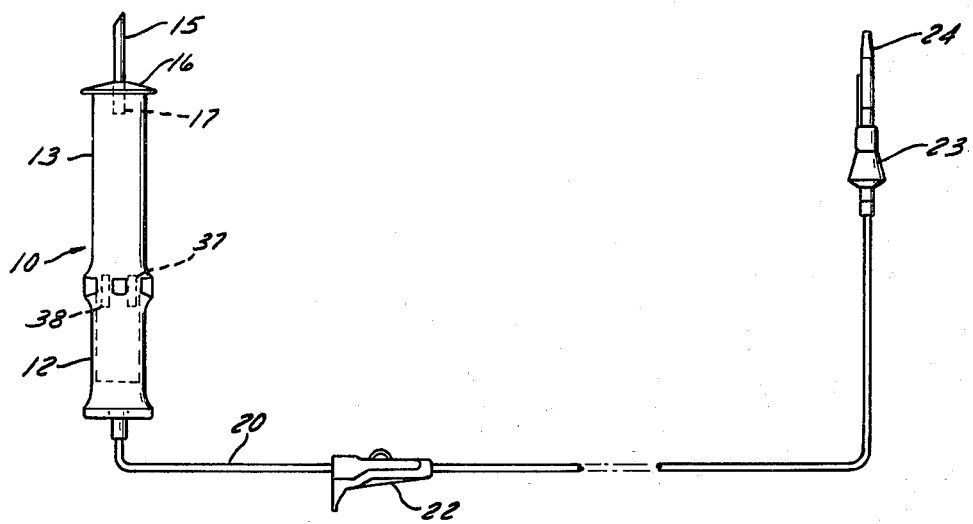
FIG. 1 is a view in side elevation illustrating the compact filter unit in combination with a filter and drip chamber and formed as a comonent of an I.V. administration set.

A combined filter and drip chamber generally 10, is shown in FIG. 1 incorporating the high capacity and compact filter unit of this invention indicated by the numeral 12. A drip chamber is shown at 13 and has the usual closure 16 with a piercing pin 15 extending therethrough. A drop forming member 17 extends into the drip chamber 13 in the usual manner. A length of tubing 20 is connected to the opposing end of the filter unit 12 and is interconnected at the opposing end to a flashback unit 23 with a needle adapter 24. The usual flow control clamp 22 is utilized in conjunction with the resulting I.V. set.

Figure 2:
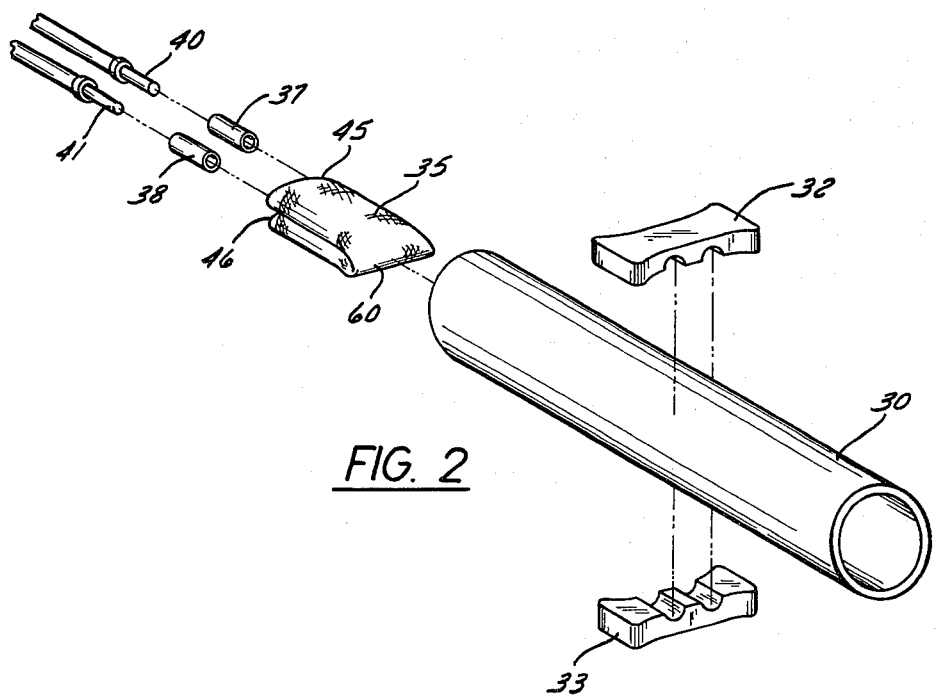
FIG. 2 is an assembly view illustrating the fabrication of the filter unit of this invention.

In FIG. 2, a folded piece of filter material 35 is illustrated to result in two filter pockets 45 and 46 separated by a common wall or fold 60. Two tubular passage members 37 and 38 are shown in orientation with the filter pockets 45 and 46, respectively. Sealing mandrels 40 and 41 are also illustrated for insertion in tubular passage members 37 and 38 for ultimate sealing of the passage members in the filter pockets inside flexible, tubular plastic 30 and this sealing is effected by Radio Frequency sealing employing sealing dies 32 and 33.

FIG. 3 illustrates the combined filter and drip chamber 10 with the tubular passage members 37 and 38 sealed therein and by means of intermediate seal 56. At the opposite end of the filter unit 12 there is an additional fluid passage member 59 which is sealed therein by means of end seal 58. That portion of the tubular plastic between seals 56 and 58 will form a closure means for sealing passage members 37, 38 and 59 therein. Seal 58 is made a distance from the fold line 60 of folded filter material 35 so as to result in a compartment 61 for the fluid material before it passes out of fluid passage member 59. Referring to FIGS. 4 and 5, it will be seen that the filter unit is initially formed from a length of tubular filter material 43, preferably composed of nylon. In this embodiment, the tubular filter material is folded into two approximately equal lengths with the common crease or wall 60 to result in the folded filter material 35 having two filter pockets 45 and 46. Into the open ends of these pockets will be placed tubular passage members 37 and 38 to be sealed therein as explained in conjunction with FIG. 2. The sealing of the filter material with the tubular passage members 37 and 38 placed therein as previously described will result in a partially fabricated unit as described in FIG. 6. The next step in the fabrication process would be the addition of fluid passage member 59 which will be sealed into tubular plastic member 30 and opposite from the two inlet passage members 37 and 38. The resulting seal 58 will be spaced from fold 60 to result in the previously referred to compartment 61. It will be recognized that seals 56 and 58 could be effected simultaneously. Solvent sealing of the closure 16 with tubular piercing pin and drop forming end 17 to plastic member 30 will next take place to result in the unit shown in FIG. 3.

FIG. 7 illustrates the placement of the folded filter material 35 in the tubular plastic member 30 with the inlet passages 37 and 38 also sealed therein. It will be noted that due to the fact that the two passage members 37 and 38 are placed in different pocket members, the filter material will assume an asymmetrical position as it is sealed in tubular member 30. For example, in relation to tubular passage members 37 and 38, a single filter wall will be positioned at opposite sides thereof such as illustrated by the numeral 50 while double walls will be oppositely positioned with respect to these tubular filter members such as shown at 52. Double pleats 54 will be effected in the filter material 43 as it is sandwiched in seal 56 both at the outside of the tubular passage members 37 and 38 as well as therebetween.

FIG. 8 illustrates the flow path of the filtered parenteral solution or blood through the filter unit 12. It will be noted that the two inlet tubular passage members 37 and 38 are in fluid communication with the two filter pockets 45 and 46 which filter pocket members are joined by the common wall or crease 60. What in effect is formed is a double filter unit which is formed in the manner of the well known flow-through teabag.

Figure 10:
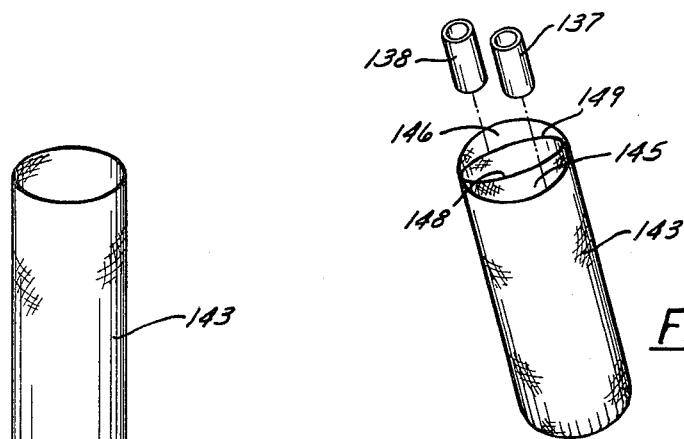
FIGS. 9-13 illustrate an alternative embodiment with FIGS. 9-13 corresponding to FIGS. 3-7, respectively.
Figure 9:
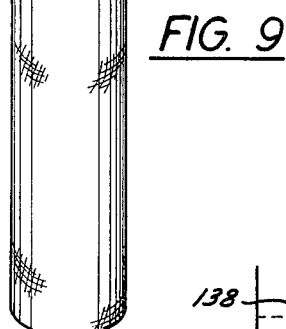
Figure 13:
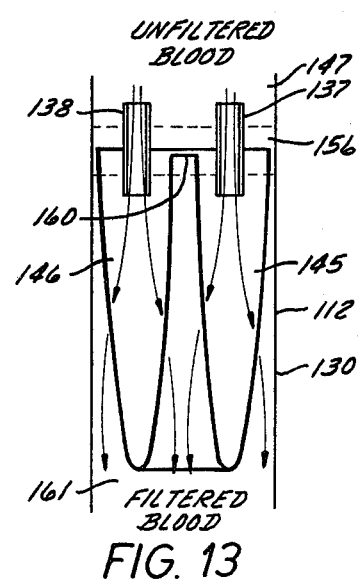
Figure 11:
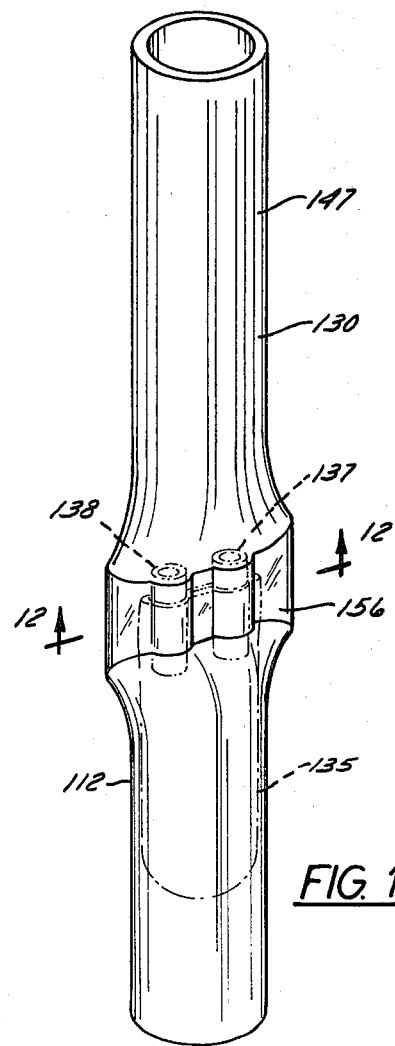
Figure 12:
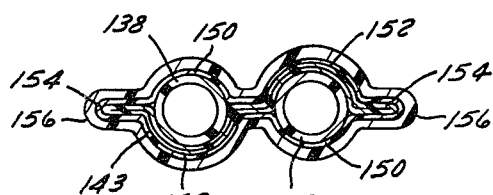

FIGS. 9-13 illustrate another embodiment of filter unit 112. Similar numbers are used to refer to similar parts except they are designated in the "00" series. The main difference between filter unit 112 and 12 is that in unit 112 filter material 143 is folded in such a manner that is is inverted so that the loose ends 148 and 149 of the filter are brought back up through and to the top thereof. This is indicated in FIG. 10. The tubular passage members 137 and 138 will then be inserted in the resulting filter pockets 145 and 146 respectively and sealed in the manner previously indicated with reference to FIG. 2. With this particular type of folding of the filter material 143 in the inverted manner, the common wall 160 will be adjacent the tubular passage members 137 and 138 rather than at the opposite end of the filter material as in unit 12.

Operation

The operation of filter units 12 and 112 should be obvious from the description previously given. It will be appreciated that filter unit 112 will also have the end of tubular member 130 opposite the inlet passages 137 and 138 and, downwardly therefrom as viewed in FIG. 11, sealed at the end with an outlet passage similar to seal 58 and outlet passage 59 in unit 12. A drip chamber similar to 13 will also be formed at the upper section 147 of tubular member 130. It will then be incorporated in an I.V. set as illustrated in FIG. 1.

When it is desired to utilize the combined drip chamber and filter unit 10, it will be interconnected with either a container or parenteral solution or blood which can be contained in a rigid or flexible container. In the instance where the container is rigid the piercing pin 15 will be vented or another source of venting supplied. As the parenteral fluid or blood drops from drop forming end 17 it will accumulate to a predetermined amount in the drip chamber 13. The liquid in this chamber then has two flow paths 37 and 38 to flow into as well as two internal filter pockets 45 and 46 to flow through all within one filter unit 12. The same flow path for the filter material will be utilized in conjunction with filter unit 112.

What in effect is accomplished is a double filter unit where a single unit was previously employed. Accordingly, for the same length of filter unit a double capacity is being effected. Further, the method of fabricating the filter unit of this invention is quite simple and can be effected without the need of extra tooling or special materials.

While the filter units 12 and 112 have been indicated for use in combination with a drip chamber, it will be readily appreciated with the drip chamber can be eliminated and the filter unit utilized by itself. All that is required would be a Y connection between the two inlet passages 37, 38 or 137 and 138 which Y connection would be connected to a single source of liquid.

The preferred material for tubular filter material 43 and 143 is nylon. However, other filter material such as polyester could be utilized. Plastic tubular members 37, 38, 137 and 138 as well as 30 and 130 are composed of polyvinyl chloride. However, other thermoplastic material such as polypropylene could be utilized. The preferred method for compressively heat sealing the filter material together is Radio Frequency. However, other compressive heat sealing methods such as hot bar welding could be employed.

It will thus be seen that through the present invention there is provided a simple filter structure which exposes a maximum of filter material with the minimum length of a filter unit for maximum filter flow. This is accomplished by having two side-by-side pocket or filter members within a single enclosure and with separate port members in individual contact with the filter pockets. The filter structure is easily fabricated with a minimum amount of steps and can be readily fabricated from existing materials which are inexpensive yet can be readily sterilized for parenteral or blood administration use. As the filter unit of this invention can be readily formed from thermoplastic materials it can be utilized in conjunction with various types of I.V. or blood sets with no critical limitations as to geometric configuration or size.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A high capacity, compact filter for the filtration of parenteral fluids comprising:
    a first filter unit;
    a second filter unit; said first and second filter units being formed from a folded, tubular mesh material and positioned in a substantially side-by-side relationship and joined by a common wall member;
    a tubular plastic member surrounding said filter units and integrally sealed to said filter units at one end and sealed closed at the opposite end to form a closure;
    a first fluid entrance passage means in fluid communication with said first filter unit;
    a second fluid entrance passage means in fluid communication with said second filter unit; and
    a fluid outlet passage member in fluid communication with said closure.

2. The filter as defined in claim 1 wherein said common wall member is positioned opposite said first and second fluid entrance passage means.

3. The filter as defined in claim 1 wherein said common wall member is positioned adjacent said first and second fluid entrance passage means.

4. The filter as defined in claim 1 wherein said first and second fluid entrance passage members and said fluid outlet passage means are defined by flexible tubular members.

5. The filter as defined in claim 1 further including a drip chamber means surrounding said first and second fluid entrance passage means in a fluid tight manner, said drip chamber means including a tubular passage means positioned opposite said first and second fluid entrance passage means.

6. The filter as defined in claim 1 wherein said closure defines a compartment opposite said passage members.

7. The filter as defined in claim 5 wherein a single seal defines the attachment of said filter units to said fluid passage means and forms the bottom of said drip chamber.

8. The filter as defined in claim 7 wherein said filter material is nylon.

9. A method of manufacturing a high capacity, compact filter for the filtration of parenteral fluids comprising:
    folding a piece of tubular mesh filter material in a manner to provide two filter pocket members positioned in a substantially side-by-side relationship;
    placing said folded tubular filter material into a length of flexible, tubular plastic material;
    inserting a mandrel member into each said filter pocket member;
    inserting a tubular fluid passage member into said length of tubular, flexible plastic material at an end opposite said mandrel member;
    and compressively sealing opposing ends of said tubular plastic material at a point where said mandrel members and said tubular passage member contact said filter material and said flexible tubular material;
    so as to seal said filter material at one end of said tubular plastic material and said fluid passage member at the opposing end thereof.

10. The method of manufacturing a filter as defined in claim 9 wherein said tubular filter is folded into two substantially equal lengths with a common crease approximately midway between the ends thereof.

11. The method of manufacturing a filter as defined in claim 9 wherein said filter material is sealed by said mandrel members in said tubular plastic material intermediate its ends and a further closure member including a drip forming member is secured to said length of flexible plastic material at an end opposite said end with said fluid passage member to provide a drip chamber.

12. The method of manufacturing a filter as defined in claim 9 wherein said tubular plastic material is sealed to said additional fluid passage member at a position spaced from said filter material so as to provide a filter compartment.

13. The method of manufacturing a filter as defined in claim 9 wherein tubular fluid passage members are inserted in each said filter pocket and sealed therein by said mandrel members, said tubular fluid passage members and said tubular plastic material are formed from a thermoplastic resinous material.

14. The method of manufacturing a filter as defined in claim 9 wherein said filter material is nylon.

15. The method of manufacturing a filter as defined in claim 9 wherein said compressive sealing is effected by radio frequency sealing.

* * * * *

UNITED STATES PATENT AND TRADEMARK OFFICE
CERTIFICATE OF CORRECTION

PATENT NO. : 4,318,812
DATED : March 9, 1982
INVENTOR(S) : John L. Vcelka, David L. Wucki It is certified that error appears in the above—identified patent and that said Letters Patent is hereby corrected as shown below:

Original Claim 13 (new Claim 11) should be added as Claim 16.

16. The method of manufacturing a filter as defined in Claim 9 wherein said tubular filter is folded in an inverted manner with one end of the filter material being drawn inside the tubular filter and all of the open ends placed adjacent each other so as to result in two filter pockets of substantially the same dimension.

On the title page

David L. Wucki, Lindenhurst, Ill. should be added as co-inventor.

Signed and Sealed this

Eleventh Day of May 1982

[SEAL]

Attest:

Attesting Officer

GERALD J. MOSSINGHOFF
Commissioner of Patents and Trademarks